United States Patent
Levis et al.

(10) Patent No.: US 9,001,325 B2
(45) Date of Patent: Apr. 7, 2015

(54) FILAMENT-BASED STIMULATED RAMAN DETECTION

(75) Inventors: Robert J. Levis, Rose Valley, PA (US); Johanan H. Odhner, Huntingdon Valley, PA (US)

(73) Assignee: Temple University —Of The Commonwealth System of Higher Education, Phila., PA (US)

( * ) Notice: Subject to any disclaimer, the term of this patent is extended or adjusted under 35 U.S.C. 154(b) by 0 days.

(21) Appl. No.: 13/983,451

(22) PCT Filed: Feb. 3, 2012

(86) PCT No.: PCT/US2012/023792
§ 371 (c)(1),
(2), (4) Date: Aug. 23, 2013

(87) PCT Pub. No.: WO2012/106608
PCT Pub. Date: Aug. 9, 2012

(65) Prior Publication Data
US 2013/0321801 A1  Dec. 5, 2013

Related U.S. Application Data

(60) Provisional application No. 61/439,847, filed on Feb. 5, 2011.

(51) Int. Cl.
*G01J 3/44* (2006.01)
*G01J 3/10* (2006.01)
*G01N 21/65* (2006.01)

(52) U.S. Cl.
CPC .... *G01J 3/44* (2013.01); *G01J 3/10* (2013.01); *G01N 21/65* (2013.01); *G01N 2021/655* (2013.01)

(58) Field of Classification Search
USPC .............................................. 356/300, 72–73
See application file for complete search history.

(56) References Cited

U.S. PATENT DOCUMENTS

| | | |
|---|---|---|
| 2002/0149842 A1 | 10/2002 | Krummrich |
| 2008/0170218 A1 | 7/2008 | Dantus et al. |
| 2008/0180655 A1 | 7/2008 | Baruch et al. |

(Continued)

FOREIGN PATENT DOCUMENTS

| | | |
|---|---|---|
| WO | 2009143351 A2 | 11/2009 |
| WO | 2010013118 A1 | 2/2010 |

OTHER PUBLICATIONS

Odhner et al; Rovibrational Wave-Packet Dispersion during Femtosecond Laser Filamentation in Air; Physical Review Letters; RPL 103, 075005 (2009).

(Continued)

*Primary Examiner* — Abdullahi Nur
(74) *Attorney, Agent, or Firm* — Drinker Biddle & Reath LLP

(57) ABSTRACT

In apparatus and methods of Raman spectroscopy in air, a target region is excited by a laser pump pulse exceeding the critical power for self-focusing in air and having a duration after self-focusing of 15 fs or less. A laser probe pulse having a duration in the range of 200 fs to 100 ps and an energy of at least 20 µJ is directed at the excited target region. Stimulated Raman scattering from the interaction between the excited target region and the laser probe pulse is detected. The target region can be outside the spectrometer, with ambient air in between used for the self-focusing.

17 Claims, 3 Drawing Sheets

Experimental Apparatus

(56) References Cited

U.S. PATENT DOCUMENTS

2009/0323058 A1\* 12/2009 Dyba .......................... 356/301
2010/0014078 A1   1/2010 Dholakia et al.
2010/0020393 A1   1/2010 Mazzio

OTHER PUBLICATIONS

Odhner et al; Filament-based stimulated Raman spectroscopy; Nonlinear Frequency Generation and Conversion: Materials, Devices, and Applications IX; Proc. of SPIE vol. 7582, 75820M1-M9.

\* cited by examiner

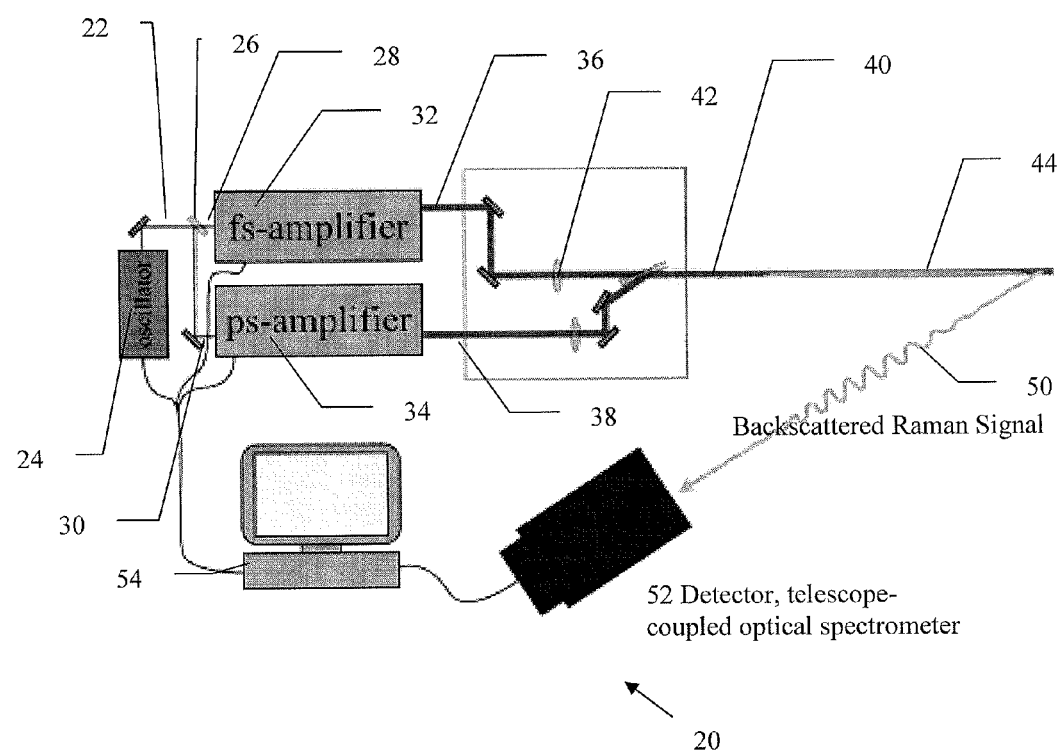
FIG. 1 – Experimental Apparatus

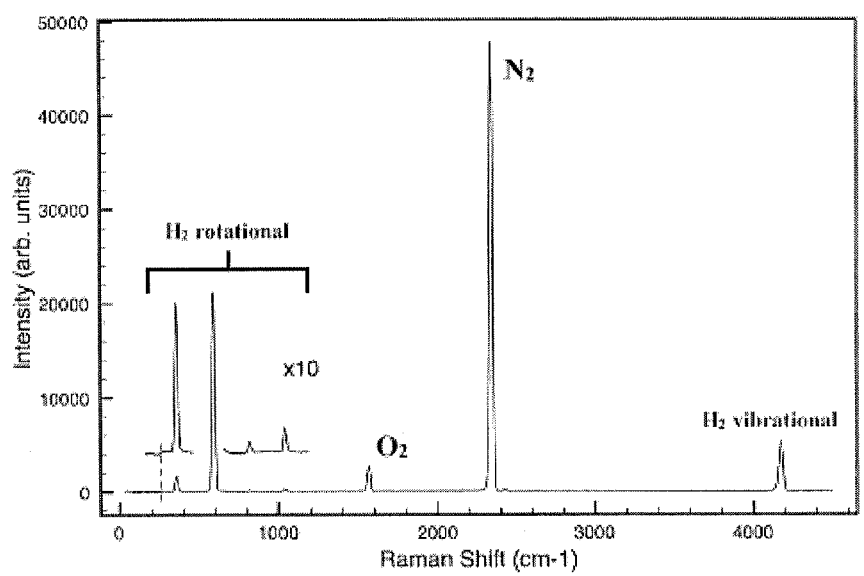
FIG. 2 – Example of single shot Raman spectrum ranging from 150 to 4600 cm-1 covering the optically active vibrational spectral range.

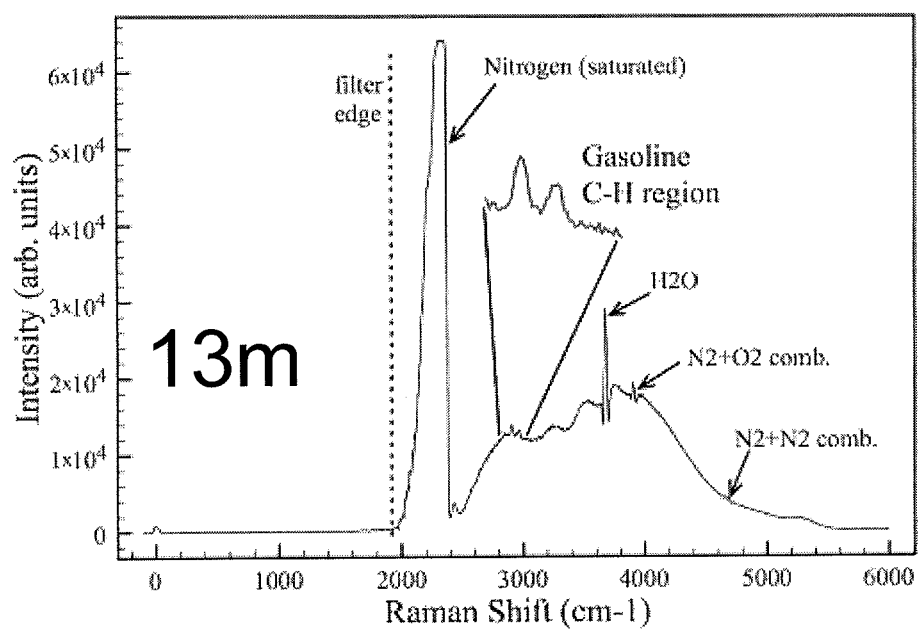
FIG. 3 – Raman spectrum of gasoline acquired at 13 meter stand off distance.

FILAMENT-BASED STIMULATED RAMAN DETECTION

CROSS REFERENCE TO RELATED APPLICATIONS

This application claims benefit of U.S. of America provisional patent application No. 61/439,847, filed on 5 Feb. 2011 by Levis and Odhner, which is incorporated herein by reference in its entirety.

STATEMENT REGARDING FEDERALLY SPONSORED RESEARCH OR DEVELOPMENT

This invention was made with government support under Award N000141010293 awarded by the Office of Naval Research. The government of the United States of America has certain rights in the invention.

BACKGROUND OF THE INVENTION

The detection of gas-phase molecules using Raman spectroscopy was at one time considered impossible. F. Calegari, et al., *Molecular rotovibrational dynamics excited in optical filamentation*, Optics Letters, Vol. 33, No. 24, 2922-2924, (Dec. 15, 2008) [3], demonstrated the use of laser filaments in argon to temporally shorten and spectrally broaden a femtosecond pump beam. The fundamental stretching mode of $H_2$ was detected, implying a pump pulse with structure smaller than 8 fs. Calegari measured his pulse width as 6.8 fs. Calegari reports detecting gas phase molecules such as $CO_2$ and $H_2$ at superatmospheric pressure. Calegari's pump and probe beams were generated by beam-splitting a single pulse with a variable delay line in the probe beam, and were thus both of fs duration. Calegari generated a time-domain sequence as a function of the pump-probe delay, and Fourier transformed that sequence to produce a frequency spectrum.

A team including the present inventors demonstrated that such molecules could be detected using an air-based filament. See Odhner, et al. Physical Review Letters, 103, 075005 (2009) [1]. Nitrogen and oxygen in air were successfully detected, using a 45 fs pump pulse shortened by filamentation, and the 8 fs hydrogen fundamental stretching mode was also detected. Odhner et al. used a 1.5 ps probe beam crossing the pump beam at a small angle, enabling a one-shot spectrum.

Further work by the same team is described in J. H. Odhner, et al., *Filament Based stimulated Raman spectroscopy*, SPIE Photonics West Conference 2010, Vol. 7582, 75820M (2010) [2].

[4] P. J. Bustard et al., *Amplification of Impulsively Excited Molecular Rotational Coherence*, Physical Review Letters, 104, 193902 (2010) [4], coupled a long (ns) probe pulse to the impulsively excited [rotational] Raman coherence generated by a short pulse. In their paper they report the sustenance and amplification of the coherent properties of the material excitation over much longer durations than would be expected without the long probe pulse.

The laser systems (oscillators and amplifiers) used in Refs. [1] to [4] are commercially available technology. The filamentation process utilized in Calegari, et al. (2008) [3] and Odhner, et al. (2009 and 2010) [1] and [2] is not commercially available technology, though the process is widely used, and is highly dependent on the input parameters of the laser beam (pulse duration and energy, as well as spatial characteristics). The choice of input parameters for filamentary pulse self-shortening is often highly specific to the working conditions of the technique.

Nonlinear pulse shortening during filamentation in noble gases as used in Calegari, et al. is a well-known and well-researched phenomenon, whereas the implementation of filamentary propagation for pulse shortening in air, as described in Odhner, et al. [1] and [2] is relatively new and is not well researched. The use of air as a propagation medium is not obvious, as it was previously thought that the molecular nature of the medium had a detrimental effect on the pulse-shortening phenomenon.

The present inventors have now discovered that filamentary propagation in air makes possible Raman spectroscopy at considerable distances from the exciting lasers, and that much higher probe pulse intensities than previously proposed make it possible to access a novel regime of coupled non-linear effects, in contrast to the single non-linear effect used in conventional stimulated Raman scattering or impulsive stimulated Raman scattering.

SUMMARY OF THE INVENTION

The present methods and apparatus make it possible to detect a wider range of gas molecules, and to detect gas molecules at much lower concentrations. Detection of molecules at concentrations in the range of parts per million or parts per billion in air would have important applications, for example, in the detection of explosives and narcotics.

A method is described for using a femtosecond laser filament to generate impulsive excitation in a molecular medium. The impulsive coherent vibrational excitation is then used for seeding and amplification of a picosecond duration probe beam using stimulated Raman scattering. The method describes a process to increase the sensitivity of coherent Raman scattering up to four orders of magnitude over current state-of-the-art vibrational Raman spectroscopy techniques described in Odhner PRL 2009 [1].

The use of a short (~10 fs, Calegari, et al. [3]) or long (0.6-1.5 ps, Odhner, et al. [1], [2]) probe pulse changes fundamentally the nature of the detected signal. In the case of a short probe pulse, the delay between the pump and the probe beams must be scanned and processed via Fourier Transform in order to recover the vibrational spectrum, which is not suitable for our application. In the case of a long probe pulse the entire vibrational spectrum is measured directly at the detector and no post-processing or scanning of the pump-probe beam delay is necessary. Both of these techniques (short pump-short probe and short pump-long probe) have been utilized previously in solid and liquid media but have been impractical until now in the gas phase. The present methods and apparatus can make it possible to obtain useful results from Raman spectra of uncompressed gases, including remote sensing of trace concentrations of vapors in ambient air.

The back-scattered Raman emission detection shown in embodiments of the present invention is made possible by the large signal intensities generated using the method described. Such detection would not have been feasible in most situations using either the Calegari (2008) [3] or the Odhner (2009 and 2010) [1], [2] methods, and was not preferable for the specific experiments published by Calegari et al. and Odhner et al. The back-scattered detection is preferable for some applications, but there might also be useful application of the in-line detection methods described in Refs. [1] to [4] as well.

BRIEF DESCRIPTION OF THE DRAWINGS

The above and other aspects, features and advantages of the present invention will be apparent from the following more particular description thereof, presented in conjunction with the following drawings. In the drawings:

FIG. 1 is a diagram of an apparatus;

FIG. 2 is an example of single shot Raman spectrum ranging from 150 to 4600 cm$^{-1}$ covering the optically active vibrational spectral range, illustrating detectable spectral lines of common gases.

FIG. 3 is a Raman spectrum of gasoline acquired at 13 meter stand off distance, illustrating the remote sensing of volatile organic vapors.

DETAILED DESCRIPTION OF PREFERRED EMBODIMENTS

A better understanding of various features and advantages of the present invention will be obtained by reference to the following detailed description of embodiments of the invention and accompanying drawings, which set forth illustrative embodiments that utilize particular principles of the invention.

In one embodiment, a laser pulse having a duration of 100 femtosecond or less with a peak power exceeding the critical power for filamentation in air is used to generate a white-light laser filament. We use, for example, a pulse having a duration of 45 fs and a per-pulse energy of 2 millijoules, corresponding to a peak power of 44 gigawatts, which is focused using a 2 meter lens in air to generate a laser filament [1]. The intrinsic temporal shortening of the pulse that occurs during the filamentation process is used to impulsively excite a collection of gas-phase molecules, resulting in coherent vibrational motion of the molecular medium. A second, picosecond-duration, laser with a power exceeding the threshold for stimulated Raman scattering is then propagated, preferably collinearly with the first laser beam, through the coherently vibrating medium, producing Raman side bands due to the interaction with the impulsively excited medium. These side bands are subsequently amplified by intra-pulse stimulated Raman scattering. The combination of these two processes leads to strong amplification of the stimulated Raman scattering process and results in a massive enhancement in sensitivity over traditional coherent Raman spectroscopic methods. The use of impulsive Raman scattering to seed and amplify the stimulated Raman scattering process represents a new form of vibrational spectroscopy.

Referring to FIG. 1, in one apparatus indicated generally by the reference number 20, the output beam 22 of a femtosecond laser oscillator 24 is split by a beamsplitter 26 into two beams 28, 30, which seed femtosecond regenerative amplifier 32 and picosecond regenerative amplifier 34, respectively. The outputs 36, 38 of the two amplifiers 32, 34 are temporally synchronized using a digital delay generator. The femtosecond beam 36 and picosecond beam 38 are then combined using a thin-film polarizer 40 for collinear propagation. The femtosecond beam 36 is focused 42 prior to the thin-film polarizer 40 to produce a laser filament resulting in the generation of a few-cycle laser pulse having a duration of ~5 fs. This pulse serves to impulsively excite all vibrations in a target medium 44 having a period of the order of the pulse length or longer, and those vibrational frequencies are specific to the chemical makeup of the molecules present in the medium 44. A 5 fs pulse is believed to excite a full spectrum of chemically significant vibrations in a typical gaseous medium 44. The picosecond beam 38 then traverses the coherently vibrationally excited medium and undergoes coherent Raman scattering to produce Raman-sidebands that are amplified by the intra-pulse stimulated Raman scattering process. This process is capable of converting a significant portion of the probe pulse energy into photons at the Stokes and anti-Stokes vibrational frequencies.

A backscattered Raman signal 50 is detected by a spectrometer 52, and the spectrum is returned to a computer 54 that controls the apparatus 20. Computer 54 may be a conventional personal computer, comprising a processor, volatile and non-volatile memory and storage for data and programs, and input and output devices.

The method is amenable to remote or point detection through measurement and recognition of the Raman spectrum of any molecule. As such this can represent a universal molecular detector. The method described enables unprecedented sensitivities for gas phase molecules, approaching part per trillion concentrations.

The laser. systems (oscillators and amplifiers) used in Refs. [1] to [4] are commercially available technology. The filamentation process utilized in Calegari, et al. (2008) [3] and Odhner, et al. (2009 and 2010) [1] and [2] is not commercially available technology, though the process is widely used, and is highly dependent on the input parameters of the laser beam (pulse duration and energy, as well as spatial characteristics). The choice of input parameters for filamentary pulse self-shortening is often highly specific to the working conditions of the technique.

Nonlinear pulse shortening during filamentation in noble gases as used in Calegari, et al. is a well-known and well-researched phenomenon, whereas the implementation of filamentary propagation for pulse shortening in air, as described in Odhner, et al. [1] and [2] is relatively new and is not well researched. The use of air as a propagation medium is not obvious, as it was previously thought that the molecular nature of the medium had a detrimental effect on the pulse-shortening phenomenon that is of interest for our Raman scattering application.

The use of a short (~10 fs, Calegari, et al. [3]) or long (0.6-1.5 ps, Odhner, et al. [1], [2]) probe pulse changes fundamentally the nature of the detected signal. In the case of a short probe pulse, the delay between the pump and the probe beams must be scanned and processed via Fourier Transform in order to recover the vibrational spectrum, which is not suitable for our application. In the case of a long probe pulse the entire vibrational spectrum is measured directly at the detector and no post-processing or scanning of the pump-probe beam delay is necessary. Both of these techniques (short pump-short probe and short pump-long probe) have been utilized previously in solid and liquid media but have been impractical until now due to limitations in available laser pulse energy. The present methods and apparatus can make it possible to obtain useful results from Raman spectra of uncompressed gases, including remote sensing of trace concentrations of vapors in ambient air.

A significant feature of the present embodiment is that the physics of the laser-matter interaction between the probe pulse and the excited medium changes substantially with increasing pulse energy. The high energy of the probe pulse (1 ps, 4 mJ@800 nm) is well beyond the traditionally weak energies used to probe the effect of the pump on the structure of the medium, and constitutes an unconventional and novel use of a high energy picosecond laser beam for femtosecond-pump/picosecond-probe systems. By coupling the high peak power femtosecond laser pulse with the high energy picosecond probe laser pulse we are accessing a novel regime of coupled nonlinear effects that has not been previously investigated. Usually methods for Raman spectroscopy limit themselves to a single nonlinear interaction effect (such as purely stimulated Raman scattering (SRS) spectroscopy or impulsive stimulated Raman scattering spectroscopy (ISRS)), and it is somewhat unintuitive to arbitrarily combine the two techniques for traditional spectroscopic applications. We believe that by coupling the two nonlinear effects we will obtain a much larger enhancement in signal than might be expected from the linear combination of two linear techniques. Bustard et al., Ref. [4], coupled a long (ns) probe pulse to the impulsively excited [rotational] Raman coherence generated by a short pulse. In their paper they report the sustenance and amplification of the coherent properties of the material excitation over much longer durations than would be expected without the long probe pulse. The possibility of amplifying the vibrational response excited by the femtosecond filament is an integral part of the method now proposed.

In the embodiment shown in FIG. 1, all three lasers described are commercially available. The femtosecond laser oscillator consists of a pump laser (in this embodiment, diode-pumped solid state technology, wavelength of 532 nm CW radiation with power between 3-10 watts) that pumps a titanium-sapphire crystal in the oscillator laser cavity. The oscillator produces an output of several hundred milliwatts of power at a nominal repetition rate of 100 megahertz. The pulse duration of the emitted laser pulses is typically several tens of femtoseconds, and the pulses are capable of being compressed to a duration of ~12-15 fs. In our implementation of the technique we used a KM Labs kit oscillator, operating at 800 nm, 84 MHz, 40 nm bandwidth. The output of the femtosecond laser oscillator is split into two pulse trains using a beamsplitter and each pulse train seeds one of the two amplifier systems, which are based on chirped-pulse regenerative amplification technology and multipass technology. The femtosecond amplifier that was used in our implementation of the method was a Coherent Legend-HE (2006 model) producing 800 nm, 40-50 fs, 2.5 mJ pulses at a 1 kHz repetition rate. The picosecond amplifier contains filters that narrow the bandwidth of the seed laser before amplification, resulting in picosecond pulse durations. The picosecond amplifier used in our implementation of the method was a Quantronix Integra-ps-HE producing 800 nm, 1-2 ps, 4 mJ pulses at a 1 kHz repetition rate. Dual seeding the femtosecond and picosecond amplifiers was necessary in this embodiment to obtain optical synchronization between the output beams.

The back-scattered Raman emission detection 50, 52 shown in FIG. 1 is made possible by the large signal intensities generated using the method described. Such detection would not have been feasible in most situations using either the Calegari (2008) [3] or the Odhner (2009 and 2010) [1], [2] methods, and was not preferable for the specific experiments published by Calegari et al. and Odhner et al. The back-scattered detection is preferable for some applications, but there might also be useful application of the in-line detection methods described in Refs. [1] to [4] as well. In our initial experiments, we have generally focused on the back-scattered detection method with long-range detection in mind. Using back-scattering, the sample being analyzed can be outside, and sometimes a considerable distance from, the entire apparatus. See, for example, FIG. 3, illustrating the detection of gasoline vapor at a 13 meter (approx. 43 feet) stand-off distance. With in-line detection, in contrast, the sample must be within the apparatus, or at least directly between different parts of the apparatus, which can give greater selectivity of what sample volume is sensed.

The frequency of the pump laser is presently believed to be largely irrelevant to the physical process of impulsive excitation, and the choice of 800 nm frequency is based on the convenience of commercially available titanium-sapphire femtosecond laser technology operating at that frequency. Similarly, the probe pulse frequency is based on the convenience of seeding the picosecond laser amplifier from the same source as the femtosecond laser amplifier, as well as the availability of commercial Ti:sapphire picosecond laser technology. As explained above, seeding the two amplifiers from a common source provides a path to obtaining the desired optical synchronization between the pump and probe pulses. The present embodiment therefore utilizes femtosecond and picosecond laser pulses that have center wavelengths of 800 nm.

The desired pulse duration and energy for the probe pulse are subject to several constraints but could cover a wide range of parameters. The constraints/requirements of these two factors are different. The pulse duration is chosen so that the resolution of the vibrational spectrum is sufficiently high as to be able to unambiguously determine the vibrations contributing to the Raman signal. The resolution required may depend on what is known a priori of the composition of the sample under examination. A pulse duration of 0.2 ps (200 fs) or 0.5 ps may be a reasonable minimum for many purposes.

A pulse duration of 1 ps gives an energy resolution in the Raman spectrum of 14.7 wavenumbers (reciprocal centimeters), corresponding to a laser line width of ~0.94 nanometers at a central laser wavelength of 800 nm (which is the output wavelength of the Ti:sapphire picosecond amplifier shown in FIG. 1). Any laser beam fulfilling this requirement of being ~1 picosecond or longer has been deemed to have sufficiently high resolution for our detection purposes in the present embodiment. Increasing the pulse duration to 2 picoseconds results in an ideal energy resolution of ~7.4 wavenumbers, which would be excellent for us. Because of the availability of 1-2 picosecond pulses from commercial Ti:sapphire systems and their sufficient energy resolution, we decided that this pulse range would be most suitable for the embodiment.

Longer pulse durations could produce finer resolution. However, beyond a certain point the increased resolution does not lead to increased accuracy in identifying real chemical species. A practical maximum may therefore be set in the range from 2 to 10 ps. The practical issue here is that maintaining the peak power (intensity) required for stimulated Raman scattering would require a large increase in pulse energy as the pulse duration is increased. We could actually go to longer pulse durations than 10 ps for the probe pulse, as there are commercially available high energy systems that operate in the ~100-200 ps pulse duration limit that might be more economical and robust on a large scale. It is realistically conceivable that the method could effectively utilize probe pulses as long as 1 ns, but at this pulse duration other considerations would come into play (practical ones, not for the interaction physics). Perhaps a reasonable maximum probe pulse duration would be 100 ps or 250 ps.

The pump pulse length for the filament may be defined as having a femtosecond duration. The most realistic range of input pump pulse durations would probably be from 25 fs to 200 fs before filamentation compression, but it is certainly possible to make a white-light filament with shorter or longer pulses. As explained above, the filamentation shortens the pulse duration, and a pump pulse duration of <8 fs, preferably around 5 fs, after compression is preferred in order to stimulate a full range of vibration modes.

Peak laser powers above a certain threshold, called the critical power for self-focusing ($P_{crit}$), are required for filament formation. The exact power depends on the properties of the propagation medium (generally air), which are not necessarily well-defined quantities. Also, the critical power for self-focusing depends on the input pulse duration, which makes it difficult to assign a single pulse energy value to the laser pulse used in the method described. It is sufficient to say that the power must be above the critical power for self-focusing in the medium, which description automatically takes into account the pulse duration/energy trade-off required to meet the specific condition.

The energy requirements of the probe pulse are a little more complicated to define. The probe pulse energy should usually be limited so as to not induce optical breakdown (ionization) of the medium to significant levels (say, <0.1%), and should usually not be so intense as to undergo nonlinear spectral and temporal pulse reshaping, as these effects would have an effect on the spectral resolution of the detection method that is usually detrimental. On the other hand, the pulse must have sufficient energy for the stimulated Raman scattering process to occur so that proper amplification of the signal beam generated by the interaction between the impulsively excited medium and the probe pulse is accomplished. In many implementations, ideally the pulse should have an available energy at or close to the upper limit on the energy defined above. Both the upper and lower energy limits are sensitive to the pulse duration and focusing conditions (range), so the specific numbers will be determined by applying these general constraints on the energy to the configuration of an individual apparatus. The minimum energy for the probe may be 1 microjoule for tight focusing, and the maximum energy may be 20 mJ for loose focusing conditions or no focusing.

The precise minimum energy at which the amplification of the coherent vibrational excitation occurs in the probe beam (as opposed to a "normal" stimulated Raman gain scenario, where the intensity of the signal grows linearly with probe pulse intensity) is dependent on the medium being probed (generally speaking, this medium is air for most practical applications relevant to the described embodiments). Practically speaking, the method can be accomplished even with very small input probe pulse energies. However, we believe that to fully utilize the method for ranged detection (which is not the only useful application of the method) would require energies in at least the tens of microjoule range. In general, probe pulse energies ranging from tens of microjoules to tens of millijoules are usually relevant to the method described here. As explained above, non-linear effects are believed to produce a disproportionate benefit when the probe pulse energy is increased above the range previously proposed in Odhner (2009) and (2010), [1], [2].

The range of pulse durations that we are defining as useful for the purpose of probing the filament is quite large, and the energies required to reach the required intensity for a given (loose) focusing scenario will vary accordingly. The peak power (defined as the pulse energy divided by the pulse duration) divided by the spatial dimension of the focused beam yields the instantaneous pulse intensity, which is the critical parameter for stimulated Raman scattering and ionization. The pulse duration, energy, and spatial dimensions defines the relevant intensity.

In one embodiment, the beam cross-section is ~6 mm$^2$ (0.056 cm$^2$). A maximum intensity of the laser pulse of ~10$^{12}$ W cm$^{-2}$ is one way of defining the limitations that we wish to impose on the probe in that embodiment, corresponding to a nominal 1 ps probe pulse duration, a per-pulse energy of 10 millijoules, and a transverse dimension of 10 mm$^2$.

The preceding description of the presently contemplated best mode of practicing the invention is not to be taken in a limiting sense, but is made merely for the purpose of describing certain general principles of the invention. Variations are possible from the specific embodiments described. For example, the references listed below describe apparatus and methods that may be combined with the teachings of the present application. Although specific embodiments have been described, the skilled person will understand how features of different embodiments may be combined.

Although the embodiments have been described with reference to filament formation, and sample detection, in air at normal atmospheric temperature and pressure, the skilled reader will understand how the principles of the invention may be adapted to other media and environments.

Thus the claims endeavor to cover the described and illustrated embodiment and modifications which come within the true intent and scope of the invention. The full scope of the invention should be determined with reference to the Claims.

References:

The following references are incorporated herein by reference in their entirety.

[1] J. H. Odhner, et al. Physical Review Letters, 103, 075005 (2009).

[2] J. H. Odhner, et al., *Filament Based stimulated Raman spectroscopy*, SPIE Photonics West Conference 2010, Vol. 7582, 75820M (2010).

[3] F. Calegari, et al., *Molecular rotovibrational dynamics excited in optical Filamentation*, Optics Letters, Vol. 33, No. 24, 2922-2924, (Dec. 15, 2008).

[4] P. J. Bustard et al., *Amplification of Impulsively Excited Molecular Rotational Coherence*, Physical Review Letters, 104, 193902 (2010),

The invention claimed is:

1. A method of Raman spectroscopy in air, comprising:
   exciting a target region by a laser pump pulse exceeding the critical power for self-focusing in air and having a duration after self-focusing of 15 fs or less and;
   directing at the excited target region a laser probe pulse having a duration in the range of 200 fs to 100 ps and an energy of at least 20 µJ;
   detecting stimulated Raman scattering from the interaction between the excited target region and the laser probe pulse.

2. The method of claim 1, wherein the energy of the probe pulse is at least 1 mJ.

3. The method of claim 1, wherein said target region is external to an apparatus, further comprising directing the pump pulse and the probe pulse from said apparatus to said target region, and detecting a backscattered Raman signal at said apparatus.

4. The method of claim 1, wherein said pump pulse is selected to generate by filamentation in air said pump pulse at said target region having said duration of 15 fs or less.

5. The method of claim 1, further comprising obtaining a spectrum of said detected Raman scattering; and identifying from said spectrum one or more gases present in said target region.

6. The method of claim 5, wherein said target region is adjacent to a solid object external to an apparatus, and wherein said one or more gases comprise volatile substances from said solid object, further comprising directing the pump pulse and the probe pulse from said apparatus to said target region, detecting a backscattered Raman signal at said apparatus, and identifying said volatile substances from said spectrum.

7. A method of Raman spectroscopy in air, comprising:
   exciting a target region external to an apparatus by directing from said apparatus to said target region a laser pump pulse exceeding the critical power for self-focusing in air and having a duration after self-focusing of 15 fs or less;

directing at the excited target region from said apparatus a laser probe pulse having a duration in the range of 200 fs to 100 ps and an energy sufficient to excite stimulated Raman scattering; and detecting at said apparatus a backscattered stimulated Raman signal from the interaction between the excited target region and the laser probe pulse.

8. The method of claim 7, wherein said pump pulse is selected to generate by filamentation in air between said apparatus and said target region a pump pulse having a duration of 15 fs or less.

9. The method of claim 7, further comprising obtaining a spectrum of said detected Raman scattering; and identifying from said spectrum one or more gases present in said target region.

10. The method of claim 9, wherein said target region is adjacent to a target object, and wherein said one or more gases comprise volatile substances from said target object.

11. A Raman spectrometer comprising:

a pump laser operative to direct through ambient air to a target region a laser pump pulse exceeding the critical power for self-focusing in air and having a duration after self-focusing of 15 fs or less;

a probe laser operative to direct at the target region a laser probe pulse having a duration in the range of 200 fs to 100 ps and an energy of at least 20 µj;

a detector operative to detect stimulated Raman scattering from the interaction between the excited target region and the laser probe pulse; and a driver operative to trigger pulses from said pump laser and then said probe laser at a time delay such that said probe laser probes said target region while said target region is excited from said pump pulse.

12. The Raman spectrometer of claim 11, wherein said driver comprises a seed oscillator, and wherein said pump laser and said probe laser comprise laser oscillators seeded by a common pulse from said seed oscillator.

13. The Raman spectrometer of claim 11, wherein the probe laser is operative to emit a pulse of at least 1 mJ energy.

14. The Raman spectrometer of claim 11, wherein said pump laser and said probe laser are positioned to direct said laser pulses out of said spectrometer to said target region, and said detector is positioned to detect a backscattered Raman signal from said target region.

15. The Raman spectrometer of claim 11, wherein said pump laser is operative to emit a laser pulse selected to generate, by filamentation in air, said pump pulse at said target region having said duration of 15 fs or less.

16. The Raman spectrometer of claim 11, wherein said detector is operative to obtain a spectrum of said detected Raman scattering; and to identify from said spectrum one or more gases present in said target region.

17. The Raman spectrometer of claim 16, wherein said detector is operative to identify from said spectrum volatile substances present in ambient air at said target region.

* * * * *